(12) United States Patent
Dubrovskyi et al.

(10) Patent No.: US 9,588,106 B2
(45) Date of Patent: Mar. 7, 2017

(54) METHODS AND COMPOSITIONS FOR MEASURING CELL PERMEABILITY

(71) Applicant: The University of Chicago, Chicago, IL (US)

(72) Inventors: Oleksii Dubrovskyi, Chicago, IL (US); Konstantin Birukov, Chicago, IL (US)

(73) Assignee: The University of Chicago, Chicago, IL (US)

( * ) Notice: Subject to any disclaimer, the term of this patent is extended or adjusted under 35 U.S.C. 154(b) by 144 days.

(21) Appl. No.: 14/019,055

(22) Filed: Sep. 5, 2013

(65) Prior Publication Data

US 2014/0065638 A1 Mar. 6, 2014

Related U.S. Application Data

(60) Provisional application No. 61/696,989, filed on Sep. 5, 2012.

(51) Int. Cl.
*G01N 33/50* (2006.01)
(52) U.S. Cl.
CPC .................................. *G01N 33/5044* (2013.01)
(58) Field of Classification Search
CPC .................................................. G01N 33/5044
See application file for complete search history.

(56) References Cited

U.S. PATENT DOCUMENTS

| | | | | |
|---|---|---|---|---|
| 5,260,210 A | * | 11/1993 | Rubin | A61K 47/48561 435/325 |
| 2002/0150927 A1 | * | 10/2002 | Matray | C07H 19/06 435/6.11 |
| 2004/0241776 A1 | * | 12/2004 | Geister et al. | 435/7.92 |
| 2005/0233965 A1 | * | 10/2005 | Schwartz et al. | 514/12 |
| 2009/0042215 A1 | * | 2/2009 | Ingham et al. | 435/7.2 |

OTHER PUBLICATIONS

Birukov et al., Magnitude-dependent regulation of pulmonary endothelial cell barrier function by cyclic stretch, American Journal of Physiology—Lung Cellular and Molecular Physiology,2003, 285(4), L785-L797.*
Duffy et al., Colorimetric Assay to Quantify Macromolecule Diffusion across Endothelial Monolayers, Biotechniques, 31:495-501 (Sep. 2001).*
Balda, et al., *J Cell Biol.* 134(4):1031-1049, 1996.
Birukov, et al., *Circ Res.* 95(9):892-901, 2004.
Birukov, *Microvasc Res.* 77(1):46-52, 2009.
Birukova, et al., *Am J Pathol.* 168(5):1749-1761, 2006.
Birukova, et al., *Am J Physiol Lung Cell Mol Physiol.* 298(6):L837-848, 2010.
Cavanaugh & Margulies, *Am J Physiol Cell Physiol.* 283(6):C1801-1808, 2002.
Cohen, et al., *Eur Respir J.* 32(4):854-861, 2008.
Crosby, et al., *Am J Physiol Lung Cell Mol Physiol.* 301(4):L536-546, 2011.
Dejana, et al., *J Cell Sci.* 121(Pt 13):2115-2122, 2008.
Fishel, et al., *Crit Care Med.* 31(8 Suppl):S502-511, 2003.
Fraser, *Free Radic Biol Med.* 51(5):967-977, 2011.
Fukuhara, et al., *Mol Cell Biol.* 25(1):136-146, 2005.
Giaever & Keese, *Proc Natl Acad Sci U S A.* 81(12):3761-3764, 1984.
Green, et al., *Biochem J* 1963; 89:599-609.
Hirase & Node, *Am J Physiol Heart Circ Physiol.* 302(3):H499-505, 2012.
Le Guelte, et al., *Biol Cell.* 103(12):593-605, 2011.
Lionetti, et al., *Curr Opin Crit Care.* 11(1):82-86, 2005.
Lo, et al., *Exp Cell Res.* 250(2):576-580, 1999.
Makena, et al., *Am J Physiol Lung Cell Mol Physiol.* 299(5):L711-719, 2010.
Maniatis, et al., *Vascul Pharmacol.* 49(4-6):119-133, 2008.
Matthay, et al., *Am J Respir Crit Care Med.* 167(7):1027-1035, 2003.
McVerry, et al., *Am J Respir Crit Care Med.* 170(9):987-993, 2004.
Mehta & Malik, *Physiol Rev.* 86(1):279-367, 2006.
Sidhaye, et al., *Proc Natl Acad Sci U S A.* 105(9):3345-3350, 2008.
Tzima, et al., *Nature.* 437(7057):426-431, 2005.
van Nieuw Amerongen, et al., *Circ Res.* 87(4):335-340, 2000.
Ware & Matthay, *N Engl J Med.* 353(26):2788-2796, 2005.
Waters & Savla, *J Cell Physiol.* 181(3):424-432, 1999.
Wojciak-Stothard & Ridley, *Vascul Pharmacol.* 39(4-5):187-199, 2002.

* cited by examiner

*Primary Examiner* — Andrea S Grossman
(74) *Attorney, Agent, or Firm* — Norton Rose Fulbright US LLP

(57) ABSTRACT

Embodiments of the present invention provide an in vitro assay that measures cell monolayer permeability. The assay utilizes detection of a binding pair initially separated by the cell monolayer as a qualitative and quantitative measure of the permeability of the monolayer. In certain embodiments, the assay is performed in the presence of a test substance that may or may not affect cell permeability. In particular aspects, the assay is performed on a substrate that is elastic. One can also assay spatial resolution of local changes by visualizing regional variations of the cell monolayers.

12 Claims, 9 Drawing Sheets

C

| | Phase contrast | FITC Fluor |
|---|---|---|
| 24 hrs |  |  |
| 48 hrs |  |  |
| 72 hrs |  |  |

METHODS AND COMPOSITIONS FOR MEASURING CELL PERMEABILITY

This application claims priority to U.S. Provisional Patent Application Ser. No. 61/696,989 filed Sep. 5, 2012, both of which are incorporated by reference in their entirety.

STATEMENT REGARDING FEDERALLY SPONSORED RESEARCH OR DEVELOPMENT

This invention was made with government support under Grant Nos. HL076259 and HL087823 awarded by the National Institute of Health (NIH). The government has certain rights in the invention.

TECHNICAL FIELD

The present invention generally concerns at least the fields of cell biology, molecular biology, and medicine.

BACKGROUND OF THE INVENTION

Changes in cell monolayer barrier integrity and compromised barrier function are key features of many pathologic conditions including atherosclerosis (Hirase and Node, 2012), cancer (Le Guelte et al., 2011), stroke (Fraser, 2011), inflammation, pulmonary edema (Fishel et al., 2003; Ware and Matthay, 2005) and others. The methods for in vitro evaluation of mass transport across the cell monolayer have wide applications in studies addressing mechanisms of cell monolayer integrity, regulation of blood-gas, blood-brain, and other barriers, as well as in drug discovery research.

Existing approaches evaluate monolayer permeability directly by measuring the amount of a labeled macromolecular tracer traveling through a cell monolayer grown on a porous filter (transwell permeability assays), or indirectly by measurements of electrical resistance across the cell monolayer under different stimulation conditions (Balda et al., 1996; Giaever and Keese, 1984). The advantage of the transwell permeability assay is its ability to test the size selectivity of intercellular barriers. Limitations include relatively low sensitivity, considerable time between measurements, low throughput format of assay, absolute requirement of complete coverage of transwell membrane by cell monolayer, fluid convection factor and diffusion characteristics of transwell membrane materials which can mask minor changes in monolayer barrier function of endothelium (Lo et al., 1999).

The advantage of electrical resistance measurements across a cell monolayer is the ability of data acquisition in real time and high sensitivity of the method. This technique however requires high cost equipment, provides indirect means for permeability evaluation, and usually uses a limited area of cell monolayer for permeability analysis.

While each existing method offers particular advantages, none allow for spatial resolution of local changes in permeability representing regional variations of endothelial and epithelial barriers in vivo, as reflected by studies of regional heterogeneity of lung injury in vivo (McVerry et al., 2004). Existing assays are also unable to evaluate permeability in endothelial or epithelial monolayers grown on elastic substrates and exposed to cyclic mechanical stretch, a key feature of ventilator induced lung injury and pathologies associated with over-distension of other organs. Embodiments described below provide for a new measurement and visualization of local permeability in cell monolayers exposed to variety of a chemical and/or mechanical stimuli.

BRIEF SUMMARY OF THE INVENTION

The present invention is directed to systems, methods, and compositions that are related to an in vitro cell permeability assay, and in particular embodiments for an in vitro cell monolayer permeability assay. There is provided herein in vitro methods for measuring permeability of a cell monolayer by assaying for binding of two binding pair members that are initially on separate sides of a cell monolayer whose permeability is to be tested.

The assay may measure cell permeability in a qualitative manner or in a quantitative manner. For example, the assay may measure a quantity of a detectable reagent(s) (including a binding pair) that directly or indirectly is indicative of cell monolayer permeability and/or the assay may qualitatively measure the presence or absence of cell monolayer permeability. The assay may measure a quantity of a detectable reagent(s) that directly or indirectly correlates to the cell monolayer permeability in the presence of a test substance and/or the assay may qualitatively measure the presence or absence of cell monolayer permeability in the presence of a test substance. In some instances, the assay detects whether or not a test substance is localized to a particular region(s) of a cell monolayer.

In embodiments of the invention, there are methods and compositions that concern high affinity interaction-based cell monolayer permeability assay. The assay may be used in any suitable capacity, including on any suitable scale, but in particular embodiments the assay may be used in a high throughput assay.

In certain embodiments, there is a technique for assaying of cultured cell monolayer integrity based on high affinity (for example, equilibrium dissociation constant (Kd) less or equal to $10^{-12}$ mol/L) interaction between two members of a binding pair. Detection of binding of the binding pair members provides permeability information about the cell monolayer. In particular embodiments, a binding pair member may comprise a macromolecule, including a polypeptide, peptide, or antibody or molecular pairs representing chelated divalent cations and poly-His peptide (for example: 6 His-peptide and IDA- or NTA-chelated peptide); or any other organic molecules capable of specifically reacting with each other through formation of covalent bound. In certain embodiments, the binding pairs encompass one ligand to one receptor binding assay. In some embodiments, FITC-avidin labeled nanoparticles of different size are used for analysis of size restriction in permeability assays; these beads bind to immobilized biotinylated matrix on a competitive basis. Conditions are such that the amount of bound beads will be proportional to efficiency of their penetration through cell-cell junctions.

A first binding pair member is attached to the surface for cultivation of cell monolayers (usually plastic or glass surface in cell culture dishes or plates), although in some cases the member is attached to a matrix that is on the surface of the substrate. Cell monolayer is grown on the top of the surface with the attached first binding pair member. For assaying of cell monolayer integrity, a second binding pair member is added to the cell culture media (on top of the cell monolayer). The state of integrity estimates are based on how many first binding pair members interact with second binding pair members. Second binding pair members either have a label itself (e.g. fluorescent or dye-conjugated) or interaction of first and second binding pair members produce a detectable signal (e.g. first binding pair member is chromogenic substrate for binding pair member).

In particular aspects of the invention, cells are grown to monolayer state on the matrix conjugated with first binding pair members (for example, biotin). Labeled second binding pair members are then added to the culture medium at the time of the permeability assay (for example, at different time points after cell stimulation with bioactive molecules). Permeability is then measured.

In embodiments of the invention, permeability testing is started with confluent cell monolayer having no or low basal permeability, and the monolayer is grown on the substrate. Adding FITC-avidin tracer (as the labeled second binding pair member, for example) to this monolayer gives a reading of an initial condition. In a parallel plate or culture well, one adds bioactive substance that may change basal permeability: it may either increase (by example, stimulation with thrombin) or decrease (by example, stimulation with prostacyclin, iloprost, barrier protective oxidized phospholipids) cell permeability. After selected time of incubation with one or more bioactive compounds (minutes to hours, for example), one adds the exemplary FITC-avidin tracer (for example, for 3 min) and after a quick washout step determines the amount of FITC-avidin bound to biotinylated gelatin (or other substrate) beneath the cell monolayer using a microplate reader or by fluorescence microscopy. One assays for FITC label accumulation in the areas of disrupted cell-cell junctions.

In specific embodiments, there is a detection system for visualization of at least one of a binding pair and particularly for visualization of binding of one member of a binding pair to another. Binding pair embodiments include surface-immobilized high affinity acceptor (for example, biotinylated gelatin) and soluble fluorescently labeled ligand, such as a dye-labeled ligand (for example, avidin). In certain aspects there is surface-immobilized enzyme (for example, luciferase or beta-galactosidase) and soluble added substrate.

In some embodiments, there is spatial resolution of local changes in permeability that represents regional variations of endothelial and epithelial barriers in vivo. In some embodiments, there is measurement of local permeability at a subcellular level in cells, including cells that are models of pathological conditions, such as agonist- and ventilator-induced lung injury.

In particular aspects there is image analysis of permeability at a subcellular scale that allows for analysis of cell permeability at single cell resolution; in certain aspects this is useful for studies using cells transfected with specific mutant proteins, for example VE-cadherin and Rho-kinase. In some cases one can utilize the system for simultaneously analyzing size-dependent permeability by using tracers of different sized labeled with different color fluorescent probes.

In certain cases, the cell monolayer permeability assay employs a substrate that is a microelectrode. Measurements of electrical resistance across the cell monolayer may be determined, such as in cases where the cell monolayer resides between two microelectrodes. In particular aspects, measurements of transendothelial electrical resistance across a cell monolayer (such as an endothelial monolayer) may be performed with the assay.

In additional embodiments, evaluation of permeability in endothelial and/or epithelial involves monolayers grown on elastic substrates and that are exposed to mechanical stretch, including cyclic mechanical stretch in at least some cases. Aspects of some embodiments provide measurement of permeability of cells (including localized permeability) exposed to mechanical strain, and in some cases, to mechanical strain and chemical stimuli.

In some embodiments, one can obtain high resolution visualization of permeability sites in the cell monolayer and its relation to local changes in cytoskeleton or cell adhesion structure. For example, one can measure the structural integrity of cell-cell junctions in addition to cell permeability assays of the invention. For example, one can identify the location of particular junction proteins to evaluate the structural integrity of cell-cell junctions. Localization of such proteins may be visualized by any standard means in the art, but in some aspects one can utilize live imaging of recombinant proteins fused with GFP-; RFP-, mCherry- or other fluorescent tag proteins; or conventional immunostaining of one or more cell junction protein(s) after a cell fixation step. Exemplary proteins include the adherens junction proteins of cadherins, p120, $\beta$-catenin, gamma-catenin, or $\alpha$-catenin. An exemplary adherens junction protein is VE-cadherin. Cytoskeleton may be visualized by immunofluorescent staining of F-actin or tubulin, or live imaging of cell monolayers expressing fluorescently tagged recombinant tubulin, actin, actin-binding construct LifeAct, etc. One can determine whether or not the localization pattern of cell-cell junctions is similar or not to the cell permeability pattern that is visualized with methods of the invention.

In particular embodiments, the cell permeability of a particular monolayer is determined using detection of binding of a pair of binding members in the assay method in the absence of any test substance that would impact cell permeability of the natural state of the monolayer. In other embodiments, the cell permeability of a particular monolayer is determined using detection of binding of a pair of binding members in the assay method in the presence of a test substance that may impact cell permeability of a monolayer. The test substance may enhance the barrier state of the monolayer, or the test substance may decrease the barrier state of the monolayer. The test substance may be said to increase or decrease permeability based on the outcome of the assay. In some cases, the ability of a test substance to increase or decrease permeability may be known, whereas in other cases the ability of the test substance is not known. Thrombin can decrease permeability in epithelial cell lines, but increases permeability in endothelial cells, for example.

The cell permeability methods discussed herein may be utilized in a chronic manner, for example to test for (such as monitor) cell permeability over the course of minutes, hours or days.

In particular cases one can measure cell permeability of transfected cells, and in at least certain aspects the cells are transfected with a vector that encodes a gene product that is known to affect cell permeability or is being tested whether or not it affects cell permeability. In some cases the gene product from the transfected cell increases permeability, whereas in some cases the gene product from the transfected cell decreases permeability. The gene product may affect cell permeability of an endothelial cell monolayer or epithelial cell monolayer, for example. In specific embodiments, the expression of the gene product is constitutively activated. In particular cases the gene product is Rho kinase or a RhoA mutant, such as RhoA-V14. Rac1 and GEF-H1 consitutively activated or dominant negative mutants and many other signaling proteins of interest.

As demonstrated herein, the Examples demonstrate absorbing the exemplary biotinylated gelatin on 96 well plates and probing monolayer integrity with FITC-conjugated avidin. This technique is useful for high throughput screening (HTS) (for example, HTS screening of small molecule libraries for compounds that modulate monolayer permeability) than any other existing techniques because of its simplicity. In addition, the assay could be used to visualize high permeability sites in the cell monolayer. This feature allows for spacial resolution of high permeability sites that existing techniques cannot perform. Another unique feature of the assay is the use of being performed simultaneously with other physical interventions of live cell monolayers (including, but not limited to cyclic stretch or shear stress), which is important in studies of pulmonary, gastrointestinal, or cardiovascular barrier dysfunction, for example. Because the first and second binding pair members interact in a dynamic manner and do not affect cell viability (e.g. luciferase-based assay), the assay proposed can be performed in real time manner and with high sensitivity.

In some embodiments, there is an in vitro method for measuring cell permeability, comprising the steps of providing a substrate comprising matrix that is contiguous to the substrate; providing a plurality of first binding pair members affixed to the polymer molecules; and providing a monolayer of cells, wherein the first binding pair members are positioned between the monolayer of cells and the layer of matrix; providing to the substrate a plurality of labeled second binding pair members capable of binding to the first binding pair members; and assaying for a measurement (qualitative and/or quantitative) of binding of the first binding pair members to the second binding pair members.

In embodiments of the invention, there is an in vitro method for measuring permeability of a cell monolayer, comprising the step of assaying for binding of a first binding pair member to a second binding pair member, said members separated by a cell monolayer desiring to be tested for permeability. In specific embodiments, the method is further defined as follows: providing an assay configuration comprising: a substrate having a matrix contiguous thereto, wherein the matrix comprises a plurality of first binding pair members; and a cell monolayer, wherein the matrix is positioned between the monolayer and the substrate; exposing to cells of the monolayer a labeled second binding pair member; and assaying for binding of the first binding pair member to the second binding pair member.

In specific embodiments of the methods, a cell monolayer is an endothelial cell monolayer or an epithelial cell monolayer. In certain embodiments of the methods, the substrate is a rigid substrate or a flexible substrate. Rigid substrates may comprise glass or plastic. Flexible substrates may comprise a silicone-based membrane, gel, PDMS, or treated rubber surface. The substrate is transparent, in some cases. In specific embodiments of the methods, the matrix comprise gelatin, collagen, fibronectin, laminin, Matrigel®, elastin, an extracellular matrix protein, or a combination thereof.

In certain embodiments of the methods, the first and second binding pair members are selected from the group consisting of biotin and avidin or a derivative thereof; protein A and fragment or constant region or immunoglobulin class G (IgG) (Fc); and glutathione S-transferase and glutathione. In cases where a binding pair member is labeled, the label may be fluorescent, luminescent, colorimetric, or radioactive.

In some embodiments of the invention, assaying for binding comprises visualizing the label through the side of the substrate that is opposite the matrix.

In some aspects of the invention, cell permeability is determined in more than one region of the cell monolayer. In specific embodiments, there is differential permeability in different regions of the cell monolayer.

In some embodiments, the methods encompass the step of exposing to the monolayer a labeled third binding pair member, wherein the labeled third binding pair member is capable of binding to the first binding pair member and is differently sized and differentially labeled compared to the labeled second binding pair member.

In specific embodiments, a second binding pair member is exposed to the cells prior to positioning of the cell monolayer in the assay configuration. In particular aspects, the second binding pair member is exposed to the cells for 0.5, 1, 2, 3, 4, 5, or more minutes prior to positioning of the cell monolayer in the assay configuration.

In some embodiments of the methods, they further comprise the step of exposing to the monolayer of cells a test substance. In particular aspects, the step of exposing the cell monolayer to a test substance occurs prior to the step of exposing the cell monolayer to the labeled second binding pair member. In at least some cases, a test substance is known to affect cell permeability of the monolayer of cells, although it may be unknown if the test substance affects cell permeability of the monolayer of cells. The test substance may increase cell permeability of the monolayer of cells, decrease cell permeability of the monolayer of cells, or have no detectable effect on permeability.

In some embodiments of the invention, the substrate is subject to mechanical stimulation prior to exposing a labeled second binding pair member to the cell monolayer. In specific embodiments, the methods further comprise the step of exposing to the monolayer of cells a test substance, wherein the substrate is subject to mechanical stimulation prior to exposing a labeled second binding pair member to the cell monolayer. Mechanical stimulation may comprise stretching of the substrate. In some embodiments, the stretching of the substrate is performed cyclically.

Some embodiments of the method further comprise the step of exposing the cell monolayer to a compound that detects a cell junction protein, such as an antibody. In some cases, the cell junction protein is an adherens junction protein.

In particular aspects of the invention, the permeability that is measured is intercellular permeability or transcellular permeability. In some embodiments, assaying for the binding of the first binding pair member to the second binding pair member occurs between cells of the monolayer. In some embodiments, assaying for the binding of the first binding pair member to the second binding pair member occurs at a cell of the monolayer. In certain aspects, the assaying step occurs after a desired period of time of exposing the cells to the labeled second binding pair member. In specific embodiments, the assaying step occurs after a desired period of time of exposing the test substance to the cell monolayer. In certain aspects, the desired period of time is minutes, hours, or days, including between five minutes and five days.

In certain aspects of the invention, the first binding pair member is an enzyme and the second binding pair member is a substrate for the enzyme, or wherein the second binding pair member is an enzyme and the first binding pair member is a substrate.

In some embodiments of the invention, there is a kit for in vitro measurement of cell monolayer permeability, said kit housed in a suitable container, comprising: a substrate; a matrix; a first binding pair member; a second binding pair member; a label; and optionally cells capable of forming a monolayer of cells. In some embodiments of the kit, the matrix is affixed to the substrate. In some aspects of the kit, the second binding pair member is labeled. In certain embodiments, the matrix is affixed to the substrate and the second binding pair member is labeled. In specific embodiments, the kit further comprises a test substance known to increase cell permeability of a cell monolayer. In some cases, the kit further comprises a test substance known to decrease cell permeability of a cell monolayer.

In some embodiments of the invention, there is a method of preparing a cell permeability assay, comprising the steps of: obtaining a substrate having a matrix contiguous thereto, wherein the matrix comprises a plurality of first binding pair members; producing a cell monolayer on the matrix; and exposing the cell monolayer to second binding pair members. In specific embodiments, the method further comprises assaying for binding of the first binding pair member to the second binding pair member. In specific embodiments, the method further comprises the step of exposing the cell monolayer to a test substance. In particular aspects of methods of the invention, the step of exposing the cell monolayer to the test substance occurs before the step of exposing the cell monolayer to the second binding pair members.

In particular embodiments, there is a control in the method that encompasses basal permeability. For example, in a 96-well format, one can utilize few (for example, 3) wells to measure basal permeability. Such a control may be referred to as a non-stimulated reference control.

In some embodiments of the invention, there is a method of screening for cell permeability capability of a test substance, comprising the steps of: providing an assay configuration comprising: a substrate having a matrix contiguous thereto, wherein the matrix comprises a plurality of first binding pair members; and a cell monolayer, wherein the matrix is positioned between the monolayer and the substrate; exposing a test substance to the monolayer; exposing to cells of the monolayer a labeled second binding pair member; and assaying for binding of the first binding pair member to the second binding pair member.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION

Figure 1:
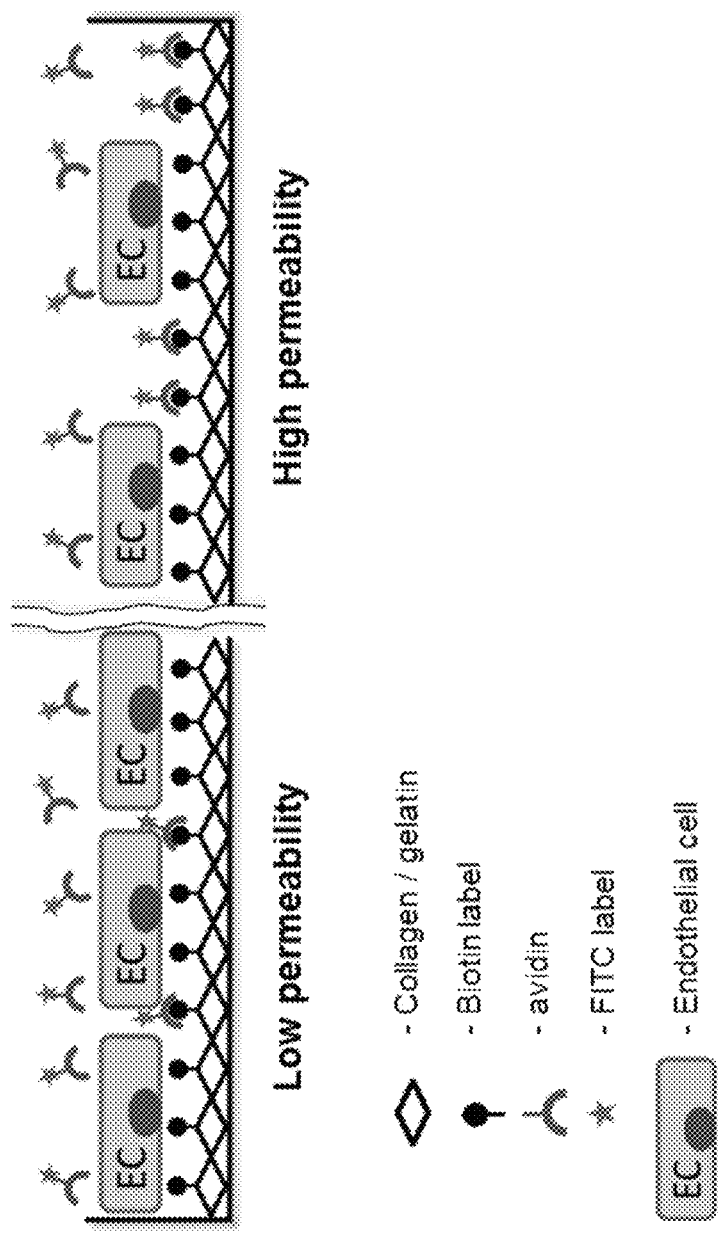
FIG. 1. Assay principle. Cells are grown on a surface coated with biotinylated adhesive matrix (i.e. gelatin or collagen-I). Permeability is assayed by direct addition of FITC-labeled avidin to the culture medium. FITC-avidin binds biotin moieties conjugated to underlying substrate and accessible through intercellular pores and openings or via transcellular mass transport pathways. The cell monolayer permeability index corresponds to the amount of FITC-avidin bound to biotinylated cell adhesive substrate.

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the invention may "consist essentially of" or "consist of" one or more elements or steps of the invention, for example. Some embodiments of the invention may consist of or consist essentially of one or more elements, method steps, and/or methods of the invention. It is contemplated that any method or composition described herein can be implemented with respect to any other method or composition described herein.

Provided herein are methods and compositions for assaying the intercellular or transcellular permeability of a cell monolayer of interest. In the assay, the cell monolayer separates two binding pair members, and the permeability property of the monolayer is determined when one of the two binding pair members permeates the cell monolayer such that it is then able to come into contact with the other binding pair member and is able to bind thereto. The binding event is detected qualitatively and/or quantitatively, providing direct information about the permeability of the monolayer itself.

In particular aspects the assay utilizes a configuration having a substrate to which a matrix is adjacent, wherein the matrix comprises one of the binding pair members. The cell monolayer desired to be tested resides on top of the matrix, and the cells of the monolayer (either before placement in the configuration or after placement in the configuration) are exposed to a labeled binding pair member. After a desired period of time, the location of the labeled binding pair member is assayed by viewing (by a variety of means) whether or not the labeled binding pair member has crossed the monolayer of cells, either between or through cells. Identification of the labeled binding pair member on the side of the cell monolayer opposite its original location (that is, the side of the cell monolayer opposite the matrix) indicates that the labeled binding pair member has permeated the cell monolayer and is binding to the corresponding binding pair member in the matrix.

I. Substrate

Embodiments include an in vitro system comprising a substrate that provides a support for the assay to be performed. In specific embodiments, the substrate is biologically inert. The substrate may be made of one or more materials and may be of any suitable material so long as it does not interact with the other components of the system, such as the cells or the matrix. In specific embodiments, the substrate is transparent, including optically transparent. The substrate is made of material that is sufficient for allowing detection of a signal from the in vitro assay system, including detection visualized from the side of the substrate that is opposite the side of the matrix.

In specific embodiments, the substrate is made of glass or plastic (including polystyrene) or rubber, for example. The substrate may be rigid or flexible.

The support may be of any physical shape that allows a suitable platform configuration for use of the assay system. In specific embodiments, the support comprises a culture dish, slide (such as a microscopy slide), wells (including 6, 12, 24, and 96-well plates), cover slips, stretch or flow chamber.

In certain embodiments, the substrate is comprised of a flexible substrate, such as an elastic substrate, for example for permeability assays in cell monolayers exposed to mechanical strain, such as cyclic mechanical strain, compression, shear stress, or increased or decreased hydraulic or atmospheric pressure. Examples of flexible supports include silicone/PDMS, Sylgard, rubber substrates, hydrogels (e.g., polyacrylamide, Matrigel), and so forth. In the elastic embodiments the cells can be grown on the surface with chemically linked biotin, or on surfaces covered with biotinylated collagen, gelatin, fibronectin, etc. In particular embodiments a silicone-based membrane is employed as an elastic substrate.

In particular embodiments a matrix for allowing fixation of one of a binding pair is attached to the surface of the substrate. Methods for affixing the matrix to the substrate are known in the art, including at least adsorption.

In certain embodiments, the substrate is a microelectrode. Published studies utilize in certain cases measurements of transmonolayer electrical resistance in cell monolayers grown on collagen- or fibronectin-coated golden microelectrode (ECIS technology). Coating microelectrodes with biotinylated substrates (e.g., collagen, fibronectin) makes possible simultaneous assessment of electrical resistance changes and visualization of high permeability spots in the cell monolayers at microscopic level A skilled artisan recognizes that some cells do not grow on metal or untreated glass (In most cases, glass surface is treated with fibronectin, collagen or gelatin prior to cell seeding) and in such cases alternative substrates are employed.

II. Cells Used in Methods

In embodiments, the permeability of a cell monolayer is assayed in an in vitro system. The cells may be of any kind, so long as they are capable of forming a monolayer or are capable of being manipulated to form a monolayer. The cells are mammalian, in certain aspects. In particular embodiments the cells are endothelial cells or normal or transformed (cancer) epithelial cells. In particular cases the cells are vascular endothelial cells, including brain, pulmonary, ocular, or microvascular endothelial cells. The epithelial cells may be also of different origin (e.g., gut, kidney, airway, endometrial, or bladder epithelial cells).

III. Matrix Layer

In embodiments, a matrix layer is present on a substrate to provide a substance to which one of a pair of binding members is attached and on which the cell monolayer resides. The matrix layer may be capable of having attached thereto a plurality of acceptor molecules (one of the binding pair member) that are not labeled and to which labeled high affinity reactants (the other of the binding pair member) are able to bind. The matrix layer does not react with the substrate or with the cell monolayer.

In particular embodiments, the matrix comprises gelatin, collagen, fibronectin, laminin, Matrigel®, elastin, ECM proteins, or a combination thereof or a combination of ECM proteins with avidin, strepavidin, enzymes such as beta-galactosidase, luciferase, or ECM proteins conjugated with 6-His peptide or Fc-fragment of antibody.

The matrix may be affixed to the substrate, such as by adsorption means that are well known in the art, or by chemical cross-linking.

In alternative embodiments of the assay, there is no matrix layer and the cell monolayer directly resides on the substrate. In such an embodiment, the high affinity ligand (one of a binding pair) is attached by chemical reaction to the substrate and is available to the other (labeled) binding pair through the permeability assay after the cells are cultured.

IV. Binding Pairs

In embodiments of the assay, there is a binding pair that is employed as part of a detection system for analyzing cell permeability. The binding of the respective members of the binding pair provide a qualitative and/or quantitative measure of the cell permeability through a cell monolayer. The binding of binding pair members is a visually or otherwise detectable event, so in particular aspects one of the binding pair members is labeled. In particular embodiments, the binding pairs are macromolecules.

In at least certain aspects the binding of the binding pair members to each other provides information about the location of cell permeability in a particular cell monolayer by assaying for location of the labeled binding pair; also, in at least certain aspects the binding of the binding pair members to each other provides information about the extent of the permeability by assaying for the amount of the labeled binding pair.

Thus, in the assay embodiments, detection reagents are utilized that include at least one set of binding pairs. In particular aspects binding pairs are utilized that do not elicit a cell stress response and are capable of binding to each other in a cell culture environment.

Examples of binding pairs include at least biotin/avidin (and avidin derivatives such as streptavidin, neutravidin, extravidin and so forth); protein A/fragment crystallizable region (Fc region); glutathione S-transferase (GST)/glutathione; quantum dots; nanoparticles (including fluorescent quantum dots, dextran, microspheres, and so forth.

In certain aspects, the binding pair provides size selectivity information about the size of permeability through the cell monolayer, such as the size of the gaps between cells. In particular aspects, two or more differentially labeled and differently sized binding pair members are assayed for the ability to permeate through the cell monolayer to bind to the target binding pair member. The differentially labeled binding members may be labeled by any means, but in specific embodiments they are labeled with differentially colored labels (including fluorescence, colorimetric, and/or enzymatic).

In particular embodiments, the unlabeled binding pair member is affixed to the matrix. The binding pair member may be affixed to the matrix in any suitable manner, dependent upon the nature of the member and/or the matrix. In particular embodiments, the binding pair member is cross-linked to the matrix. For example, biotin may be conjugated to gelatin or collagen. In particular embodiments, NH2- groups are introduced to glass surface with aminosilanation and biotinylated matrix protein (collagen or gelatin) are crosslinked to the aminosilanated glass surface.

V. Labels and Labeling

Embodiments include labeled binding pair members. The detection of the label of one of the binding pair members provides information about its location, including whether it is on one side of the cell monolayer in its unbound state at a starting position for the assay or whether it is detected on the other side of the cell monolayer as being bound to its binding pair member and as a reflection of having permeated the cell monolayer.

Labels may be of any kind so long as they are detectable. The labels may be fluorescent, colorimetric, radioactive, enzymatic, or a combination thereof. A label may also involve exchange of a photon or other energy source. The methods to affix a label to one of a binding pair are well known in the art, including by fusing, crosslinking or chelating.

VI. Exemplary Methods

Embodiments provide an in vitro assay system for measuring cell monolayer permeability. Methods that utilize the system may be employed for research, commercial, and/or industrial purposes. Cell permeability may be associated with pathologies of certain diseases. In particular aspects the in vitro assay system is employed for assaying drug testing and/or drug discovery. Exemplary research purposes include at least studies addressing mechanisms of cell monolayer integrity, regulation of blood-gas, blood-brain, and other barriers.

The system may be utilized for a high throughput assay in certain cases, including a roboticized system for rapid screening, such as for drug discovery, for example. The drug discovery may be for drugs for atherosclerosis, cancer, stroke, inflammation, pulmonary edema, and so forth.

In some embodiments, the assay is employed for assaying intercellular permeability. In some embodiments the assay is employed for assaying transcellular (transversing a cell) permeability. The assay may be employed to distinguish between intercellular and transcellular permeability. In transcellular embodiments, the labeled binding pair member is captured by vesicle and transported through the cell. Because this labeled binding pair member is trapped by the substrate under the cells, as opposed to between the cells, the transcellular permeability is determined and is distinguished from intercellular permeability. In specific embodiments, such a transcellular permeability assay is performed on gut epithelial cells, as an example, although any cells may be employed in this manner.

In certain aspects, one analyzes the outcome of the assay by analyzing the image from a visually transparent substrate from the bottom of the substrate, thereby detecting an image of the bottom (relative to the initial exposure of the cell monolayer to a labeled binding pair member) of the cell monolayer to identify whether or not the labeled binding pair member has permeated through the cell monolayer, where the member has permeated, and/or how much has permeated. However, in certain cases the bottom of the substrate may not be visually transparent, such as when the label is radioactive, for example, and the radioactivity is measured non-visually by a variety of means known in the art.

The assay may be performed in the context of permeability extent with respect to a baseline output. For example, one can measure the permeability of the monolayer in the absence of a test substance that is in need of determining its cell permeability affects; following this, one can measure the permeability of the monolayer in the presence of the test substance.

The methods may be performed with particular order of addition of reagents. For example, in particular embodiments, the cells are exposed to a test substance, a period of time lapses, and then the labeled binding pair member is added, following which it is determined whether or not the labeled binding pair member permeates through or across the cells.

In some methods, size selectivity is determined by comparing the permeability in the assay of two differentially sized molecules. For example, the two differentially sized molecules may be two differentially sized and differentially labeled binding pair members that are capable of binding the same binding pair partner in the matrix. Distinguishing whether or not one of the two differentially sized and differentially labeled binding pair members could permeate the cell monolayer (including in a localized-specific manner) provides useful information about the monolayer, including, for example, the size of the space between cells.

In certain methods that employ the assay, one can immobilize an enzyme (for example, luciferase) or enzyme substrate to the assay substrate (such as a bottom of a culture dish). Enzymatic reaction starts when a substrate reaches an enzyme. It means that if the reaction product is fluorescent or chromogenic, for example, it can be evaluated by detection in outflowing medium in microfluidics setting, thus allowing for monitoring of dynamic changes of cell monolayer barrier function in time. Once the cells reseal the gaps and restore monolayer integrity, there is less access to enzyme or substrate, the reaction decreases, and one can detect a change in permeability, including over a particular time frame, if the half-life of the product is short; an example includes luciferase.

The assay system allows detection of cell permeability under live conditions and in real time. In certain aspects, one can measure permeability after a desired period of time of exposure to a test substance, including for a duration of minutes or hours or days, for example.

VII. Kits

Any of the compositions described herein may be comprised in a kit. In a non-limiting example, an in vitro assay configuration may be comprised in a kit in suitable container means. The kit may be used for in vitro measurement of cell monolayer permeability. The kit may comprise a substrate; a matrix; a first binding pair member; a second binding pair member; a label; cells capable of forming a monolayer of cells, or a combination thereof. In some cases, the kit houses the matrix affixed to the substrate, although in some cases the user affixes the matrix to the substrate. In some cases, the second binding pair member is labeled, although in some cases the user affixes the label to the second binding pair member. Some aspects of the kit include one or more test substances, and in some cases the test substance is known to increase cell permeability of a cell monolayer, whereas in other cases a test substance is known to decrease cell permeability of a cell monolayer.

The kits may comprise a suitably aliquoted reagent. The reagents of the kits may be packaged either in aqueous media or in lyophilized form. The container means of the kits may include at least one vial, test tube, flask, bottle, syringe, box, or other container means, into which a component may be placed, and preferably, suitably aliquoted. Where there are more than one components in the kit, the kit also will generally contain a second, third or other additional container into which the additional components may be separately placed, where appropriate. However, various combinations of components may be comprised in a vial. The kits also will typically include a means for containing the components and any reagent container in close confinement for commercial sale. Such containers may include injection or blow-molded plastic containers into which the desired vials are retained. However, the components of the kit may be provided as dried powder(s). When reagents and/or components are provided as a dry powder, the powder can be reconstituted by the addition of a suitable solvent. It is envisioned that the solvent may also be provided in another container means.

EXAMPLES

The following examples are included to demonstrate certain embodiments. It should be appreciated by those of skill in the art that the techniques disclosed in the examples which follow represent techniques discovered by the inventor to function well in the practice of certain embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of embodiments.

Example 1

Measurement of Local Permeability at Subcellular Level in Cell Models of Agonist- and Ventilator-Induced Lung Injury Alterations of cell monolayer integrity and increased vascular permeability are associated with many pathologies including atherosclerosis, stroke, lung injury, cancer, digestive disorders and others. Current approaches to probe cell permeability require specific culture conditions and provide an average estimation of trans-monolayer permeability, while analysis of regional monolayer permeability in static and mechanically challenged monolayers at a single cell scale resolution remains unavailable. Provided herein is a new approach for visualization and rapid quantitation of trans-monolayer permeability based on high affinity interactions between substrate-bound acceptor and ligand in the culture medium. As demonstrated in the following Examples, general and local permeability responses to a spectrum of barrier protective and barrier disruptive agonists and their combinations were simultaneously evaluated in endothelial cell (EC) monolayers and revealed the paracellular pathway as the predominant mechanism of agonist-induced mass transport by pulmonary EC. Provided herein is demonstration of detection for the first time in a direct assay of a synergistic effect of pathologic cyclic stretch related to ventilator induced lung injury (VILI) and thrombin in the development of pulmonary EC hyper-permeability response associated with VILI. The spectrum of substrates, assay formats and experimental conditions compatible with this assay indicates its broad application in the areas of endothelial and epithelial biology, cancer research and other fields.

Example 2

Exemplary Materials and Methods

Reagents.

Chemicals and reagents including collagen type-I (cat. #C3511) and gelatin (cat. # G2500) were obtained from Sigma-Aldrich (St. Louis, Mo.) unless noted otherwise. FITC-avidin and Texas-Red phalloidin and all reagents for immunofluorescence staining were obtained from Molecular Probes (Eugene, Oreg.). EZ-Link NHS-LC-LC-Biotin (cat. #21343) was purchased from Thermo Scientific (Rockford, Ill.). 8-Bromo-adenosine-3',5'-cyclic monophosphate (8Br-cAMP) was purchased from EMD Millipore (Billerica, Mass.). Non-oxidized 1-palmitoyl-2-arachidonoyl-sn-glycero-3-phosphorylcholine (PAPC) was obtained from Avanti Polar Lipids (Alabaster, Ala.). Oxidized PAPC (Ox-PAPC) was obtained by exposure of dry lipid to air followed by mass-spectrometry analysis (Birukov et al., 2004). cMyc antibody was purchased from Santa Cruz Biotechnology (Santa Cruz, Calif.); VE-cadherin antibody was purchased from Cayman (Ann Arbor, Mich.). 96-well polystyrene plastic cell culture certified plates (Costar 3596) were purchased from Corning (Corning, N.Y.). 6-well culture plates with stretchable silicon-based membrane (BioFlex amino-treated plates) were purchased from Flexcell International (Hillsborough, N.C.). Rinzle plastic coverslips (cat. #72261-18) were purchased from Electron Microscopy Science (Hatfield, Pa.).

Human Pulmonary Artery Endothelial Cell Culture.

Human pulmonary artery endothelial cells (HPAEC) were obtained from Lonza (Allendale, N.J.) and cultured in cell growth medium (EGM-2, Lonza) containing 10% fetal bovine serum (FBS). Cell cultures were maintained at 37° C. in a humidified 5% $CO_2$ incubator and used for experiments at passages 5-8. In experiments with agonist stimulation, 10% FBS growth medium was replaced with 2% FBS growth medium for 2 hours prior to experiment. Measurements of transendothelial electrical resistance across a confluent endothelial cell monolayer were performed using the electrical cell-substrate impedance sensing system ECIS-1600 (Applied Biophysics, Troy, N.Y.). Transient transfections with cMyc-tagged RhoA-V14 or Rho kinase-CAT (6-553) were performed using PolyJet transfection reagent (SignaGen, Rockville, Md.) according to the manufacturer's protocol. In brief, HPAEC were seeded on 35 mm diameter cell culture dishes with biotinylated gelatin-treated coverslips at a density of $5 \times 10^5$ cells per dish. After 24 hours cells were transfected with 1 µg of plasmid DNA per dish (ratio: 1 µg of DNA per 3 µl of PolyJet). Permeability visualization experiments were performed 24 hours after transfection.

Gelatin/Collagen Biotinylation and Adsorption on Polystyrene Surfaces and Silicon-Based Membranes Gelatin from porcine skin (G 2500, Sigma, St. Louis, Mo.) was dissolved in bicarbonate buffer (0.1 mol/L $NaHCO_3$, pH 8.3) to a final concentration 10 mg/ml. The mixture was placed on 70° C. water bath with constant stirring for complete gelatin dissolution. The solution was clarified by low speed centrifugation (10,000×g, 5 min, room temperature). EZ-Link NHS-LC-LC-Biotin dissolved in DMSO (5.7 mg/ml) was added to gelatin solution at 0.57 mg/ml final concentration. The biotin conjugation to gelatin was performed for 1 hour at room temperature with constant stirring. Biotinylated proteins were stored in aliquots at −20° C. For gelatin adsorption, an aliquot of biotinylated gelatin was thawed in 37° C. water bath for 10 min, diluted with 0.1 mol/L bicarbonate buffer, pH 8.3 to a final concentration 0.25 mg/ml, sterilized by filtering through 0.22 µm filter and added to culture plates/wells. For 96-well plate format, 50 µl of biotinylated gelatin per well was added; for BioFlex plate, 3 ml per well was added; for 35 mm culture dishes, 2 ml per dish was added. The biotinylated gelatin adsorption was performed at 4° C. overnight. After protein adsorption plates/dishes were washed twice with PBS (pH 7.4, 200 µl per well), and cells were plated at the desired density. If short-term storage was required, plates/dishes were left in PBS and stored at 4° C. for up to two weeks.

To optimize FITC-avidin binding efficiency to the biotinylated gelatin, the latter was diluted in PBS and used in the 0.08 mg/ml-10 mg/ml concentration range. 50 µl of solution was added to each well in a 96-well plate and adsorbed overnight at 4° C. After the adsorbtion step, the plate was washed twice with 200 µl of PBS (37° C.). Serial dilutions of 2.5 mg/ml FITC-avidin stock solution were prepared in PBS. 100 µl of FITC-avidin solution was added to each well in the 96-well plate and the binding reaction was performed for 1 min at room temperature. Unbound FITC-avidin was removed by two rounds of plate washing with PBS (200 µl per well).

96-Well Assay

For the permeability assay in the 96-well plates, cells were seeded on biotinylated gelatin-coated plates ($3 \times 10^4$ cells/well) and grown for 48-72 hours prior to testing. FITC-avidin solution was added directly to the culture medium at the final concentration 25 µg/ml for 3 min before termination of the experiment unless otherwise specified. Unbound FITC-avidin was washed out with 200 µl PBS, pH 7.4, 37° C. (two cycles, 10 sec each). Finally, 100 µl PBS was added in each well, and the fluorescence of matrix-bound FITC-avidin was measured on Victor X5 Multilabel Plate Reader (Perkin Elmer, Waltham, Mass.) using an excitation wavelength of 485 nm and emission wavelength of 535 nm, 0.1 sec.

Permeability Visualization

Permeability visualization experiments were performed on 18×18 mm square Rinzle plastic coverslips. The coverslips, placed in 35 mm culture dishes, were coated with biotinylated gelatin as described above. HPAEC were seeded ($4.5 \times 10^5$ cells/dish) and grown for 48-72 hours to reach confluence. Cells were transferred to EGM-2 containing 2% FBS two hours prior to agonist stimulation. At the time point of permeability evaluation, FITC-avidin (25 µg/ml final concentration) was directly added to the culture medium for 3 min followed by two washing steps (3 ml of PBS, pH 7.4, 37° C.) and cell fixation with 3.7% formaldehyde in PBS (10 min, room temperature). Immunofluorescence staining of F-actin, VE-cadherin and tagged overexpressed proteins was performed as described elsewhere (Birukova et al., 2010). Images were acquired using Nikon video imaging system Eclipse TE 300 (Nikon, Tokyo, Japan) equipped with a digital camera (DKC 5000, Sony, Tokyo, Japan); 10× and 60× objective lenses were used. Images were processed with Adobe Photoshop 7.0 software (Adobe Systems, San Jose, Calif.).

Permeability Measurement During Cyclic Stretch

Cyclic stretch (CS) experiments were performed using FX-4000T Flexcell Tension Plus system (Flexcell International, Hillsborough, N.C.) equipped with 25 mm BioFlex Loading station, as previously described (Birukova et al., 2010). Coating of BioFlex plates with biotinylated gelatin was performed as described above. Cells were seeded at density $5 \times 10^5$ cells per well and grown for 48-72 hours to reach confluence. Cells were exposed to high magnitude cyclic stretch (18% distension, sinusoidal wave, 25 cycles/ min) to recapitulate the mechanical stress experienced by the alveolar endothelium during mechanical ventilation at high tidal volume. After two hours of CS stimulation cells were treated with vehicle or thrombin under continuing cyclic stretch. Control BioFlex plates with static cell culture placed in the same cell culture incubator and processed similarly to the stretch-preconditioned cells were used as control. At the end of the experiment, FITC-avidin (final concentration 25 µg/ml) was added to the culture medium for 3 min. Unbound FITC-avidin was removed by two-step washing with 3 ml of PBS (37° C.). Elastic bottoms of BioFlex plates with HPAEC were excised with a scalpel and transferred to a polystyrene 6-well cell culture plate. Each membrane was covered with 1 ml of PBS and the fluorescence of membrane-bound FITC-avidin was measured with Victor X5 Multilabel Plate Reader as describe above.

Statistical Analysis.

Results are expressed as mean±SD. Experimental samples were compared to controls by unpaired Student's t-test. For multiple-group comparisons, a one-way analysis of variance (ANOVA) and Tukey's post hoc multiple-comparison test were used. $P<0.05$ was considered statistically significant. Ten independent experiments were performed to evaluate effects of protective and barrier disruptive agonists in 96-well assay format; three independent experiments were performed to demonstrate the thrombin time course in 96-well assays; four independent experiments were done for VE-cadherin/FITC visualization; three independent experiments for cMyc-tag/FITC visualization, and five independent cyclic stretch-permeability experiments were performed. All measurements were performed in triplicates.

Example 3

The Concept of XPerT Permeability Assay

To overcome the drawbacks of existing technologies, a culture plate surface underlying growing cells was utilized as a permeability detection surface. In this assay, the permeability is measured as the bulk amount of the fluorescently labeled ligand FITC-avidin) bound to the surface-immobilized high affinity acceptor underneath the cell monolayer (FIG. 1).

In the prototype assay, biotinylated gelatin absorbed on a polystyrene or silicon-based surface was used as the detection surface, and FITC-labeled avidin was used as the permeability tracer. This selection was dictated by 1) high affinity acceptor-ligand interaction ($K_d \approx 10^{15}$) in most biological buffers (Green, 1963); 2) flexibility of biotinylation techniques that can be applied to different substrates; and 3) wide range of chemical conjugates of avidin and its bacterial analog streptavidin which can be used for various modes of detection (i.e. multicolor fluorescent or enzymatic-based assay platforms).

Assay Optimization and Testing in Cell Culture

Figure 2:
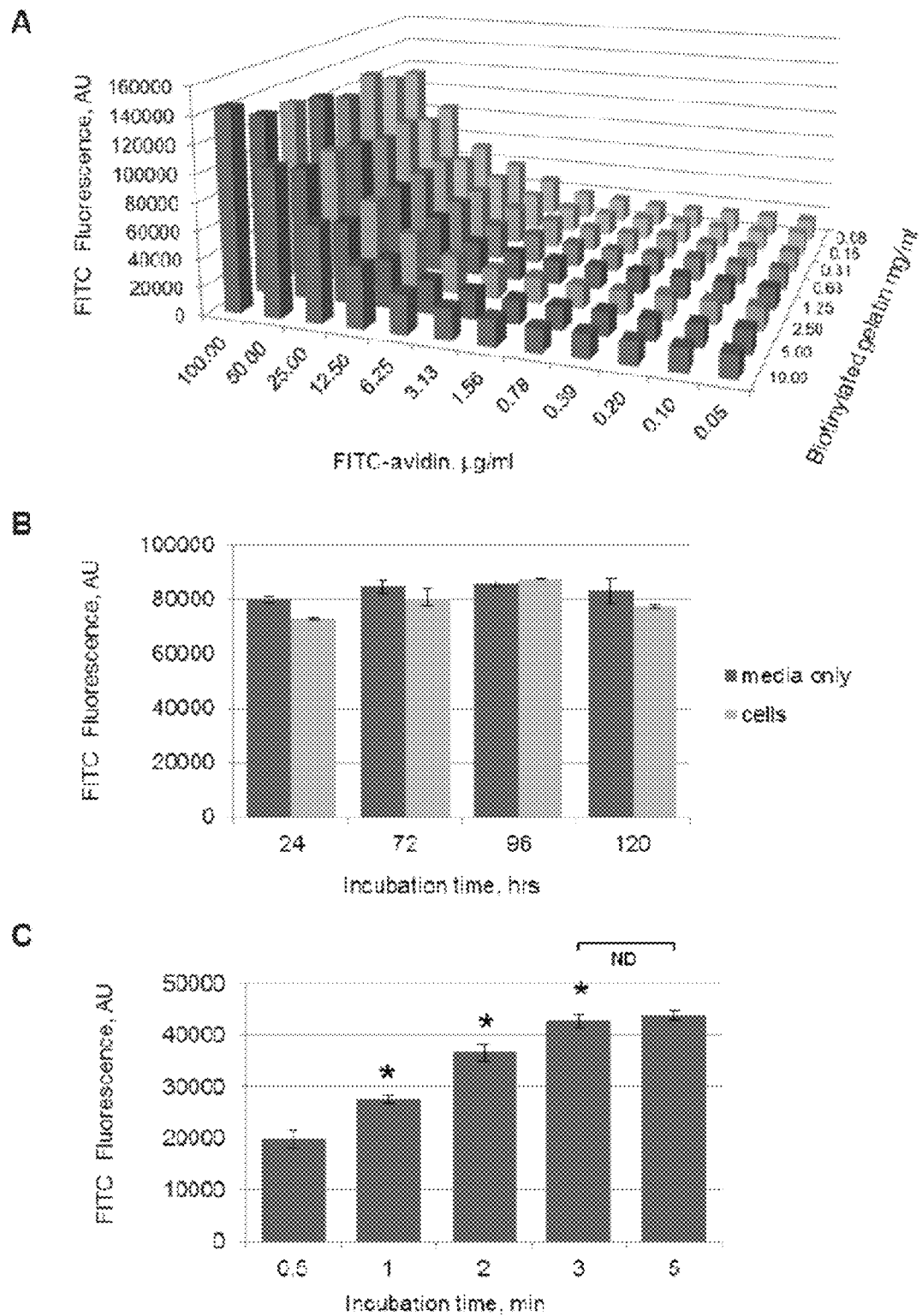
FIG. 2. Assay optimization. A—Titration of FITC-avidin—biotinylated gelatin binding ratio. Gelatin was biotinylated as described in the Methods and adsorbed on a 96-well polystyrene plate at the indicated concentrations. FITC-avidin at the 50 µg/ml-0.024 µg/ml concentration range was added to the assay plate (100 µl per well) for 1 min at room temperature. Unbound FITC-avidin was removed, and FITC fluorescence at the bottom of culture dish measured. B—Effect of cell culture on the FITC-avidin binding capacity of surface-adsorbed biotinylated gelatin. HPAEC were cultured in a 96-well plate coated with biotinylated gelatin (0.25 mg/ml, overnight incubation) for 24, 72, 96, or 120 hours. At the end of cell incubation time, cells were detached by treatment with 50 mM EDTA in PBS (37° C., 10 min), and measurements of FITC-avidin binding capacity of cell-preconditioned substrate were performed. Plates coated with biotinylated gelatin and similarly processed without HPAEC culturing served as controls. C—Optimization of FITC-avidin incubation time for detection of thrombin-induced permeability. HPAEC grown in 96-well plates with immobilized biotinylated gelatin (0.25 mg/ml) were treated with 0.3 U/ml of thrombin (15 min), and FITC-avidin (25 µg/ml) was added for the indicated time periods. Unbound FITC-avidin was removed, and FITC fluorescence was measured.

Titration experiments defined the optimal adsorbtion of biotinylated gelatin to the polysterene multiwell plates which was tested by quantification of FITC-labeled avidin bound to biotinylated gelatin-coated cell-free 96-well plates (FIG. 2A). Adsorbtion of biotinylated gelatin reached plateau levels at 0.08 mg/ml. FITC-labeled avidin at a concentration of 25 µg/ml was used in the following studies (FIG. 2A). Initial tests showed that binding of soluble FITC-biotin conjugates to avidin immobilized on the plastic surfaces was less efficient and reliable, although this can be optimized by standard means in the art. Biotinylated gelatin-coated culture plates were further tested in cell culture experiments.

Because a certain time is required for cell attachment, spreading and formation of a continuous cell monolayer, it is possible that growing cells can degrade the underlying biotinylated substrate and compromise the sensitivity of the assay. These potential effects were tested using human pulmonary endothelial cells (HPAEC) grown during 24, 72, 96 and 120 hrs in multiwell plates coated with biotinylated gelatin (0.25 mg/ml). The FITC-avidin binding capacity of cell-preconditioned biotinylated gelatin matrix was evaluated after cell removal with 50 mM EDTA and addition of FITC-avidin at saturating concentration. Cell preconditioning for up to 120 hrs showed no effect on the FITC-avidin binding capacity to the adsorbed biotinylated gelatin (FIG. 2B). Similar results were obtained with immobilized biotinylated collagen-I. These data indicate high signal stability during cell growth in this assay.

The time window of cell monolayer incubation with FITC-avidin for optimal detection of permeability was further defined. Cells were stimulated with thrombin for 15 min, and FITC-avidin was added for 30 sec, 1 min, 2 min, 3 min or 5 min before the termination of the experiment and fluorescence measurements. The three minute incubation with FITC-avidin provided the optimal fluorescence signal reflecting the cell monolayer barrier state (FIG. 2C).

The optimal conditions of cell permeability assays defined in these optimization experiments were used in all subsequent experiments (immobilization of biotinylated gelatin –0.25 mg/ml, 18 hrs, +4° C.; permeability detection by 3 min addition of 25 µg/ml FITC-avidin. Cells were grown on the biotinylated gelatin for 24-48 hrs prior to permeability testing.

Example 4

Application of XPerT for High Throughput Screening

Figure 3:
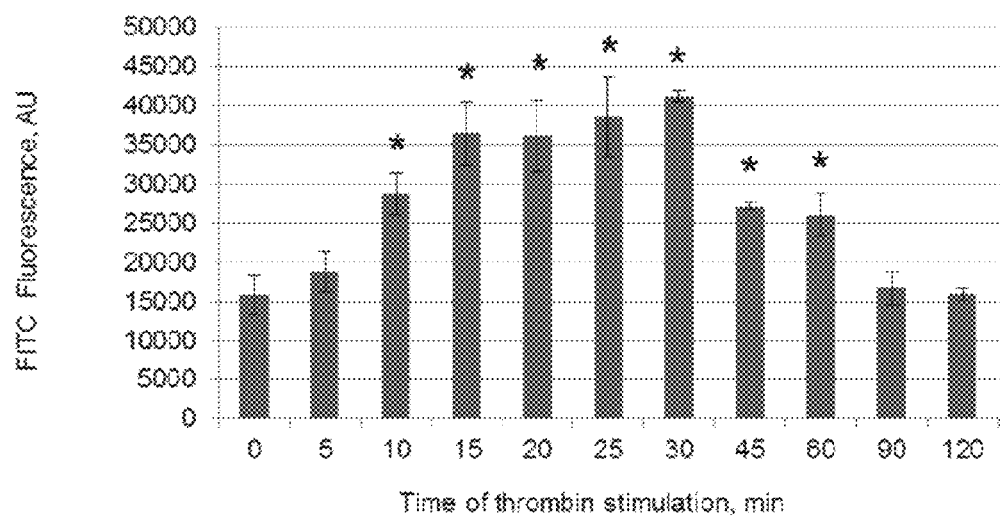
FIG. 3. Fluorimetric evaluation of monolayer permeability in 96-well plates. A—HPAEC were treated with 0.3 U/ml of thrombin for indicated time periods followed by permeability analysis using measurements of FITC fluorescence. *P<0.05 vs. control. B—Cells were pretreated with vehicle, thrombin (0.3 U/ml) for 15 min, or OxPAPC (15 µg/ml), 8Br-cAMP (500 or forskolin (2 µM) for 30 min. Alternatively, cells preincubated for 30 min with OxPAPC, 8Br-cAMP, or forskolin were stimulated with thrombin (0.3 U/ml, 15 min). *P<0.05 vs. control; #P<0.05 vs. thrombin alone. C—Measurements of transendothelial electrical resistance across confluent HPAEC were performed as described in the Methods. Bar graph represents normalized cell monolayer resistance measured in the same conditions as panel b. *P<0.05 vs. thrombin alone. FITC-avidin binding correlates with measurements of transendothelial resistance.
Figure 3:
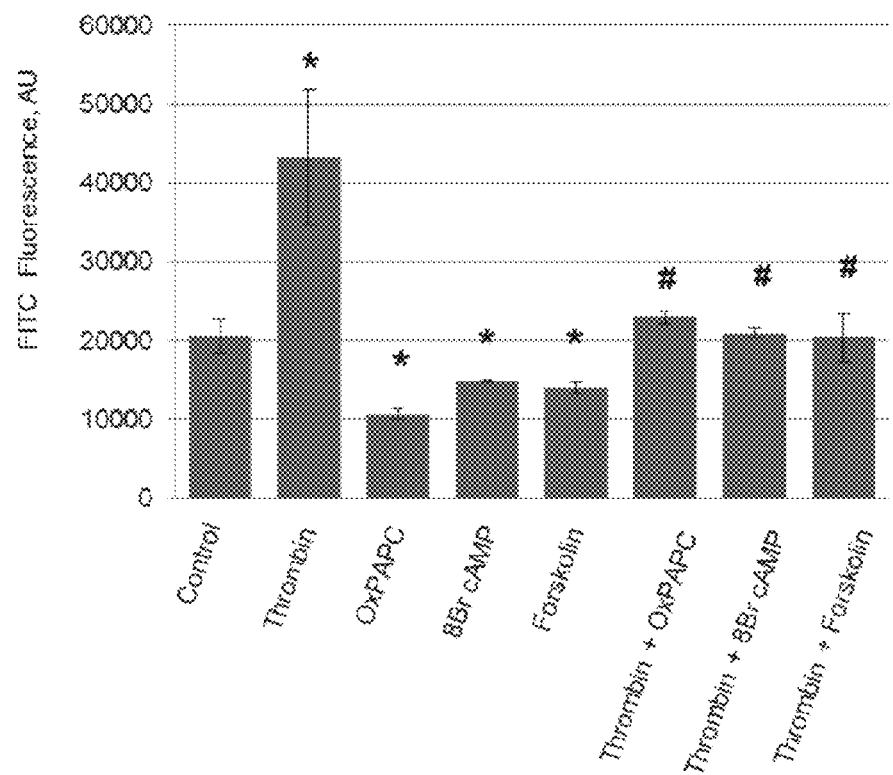
Figure 3:
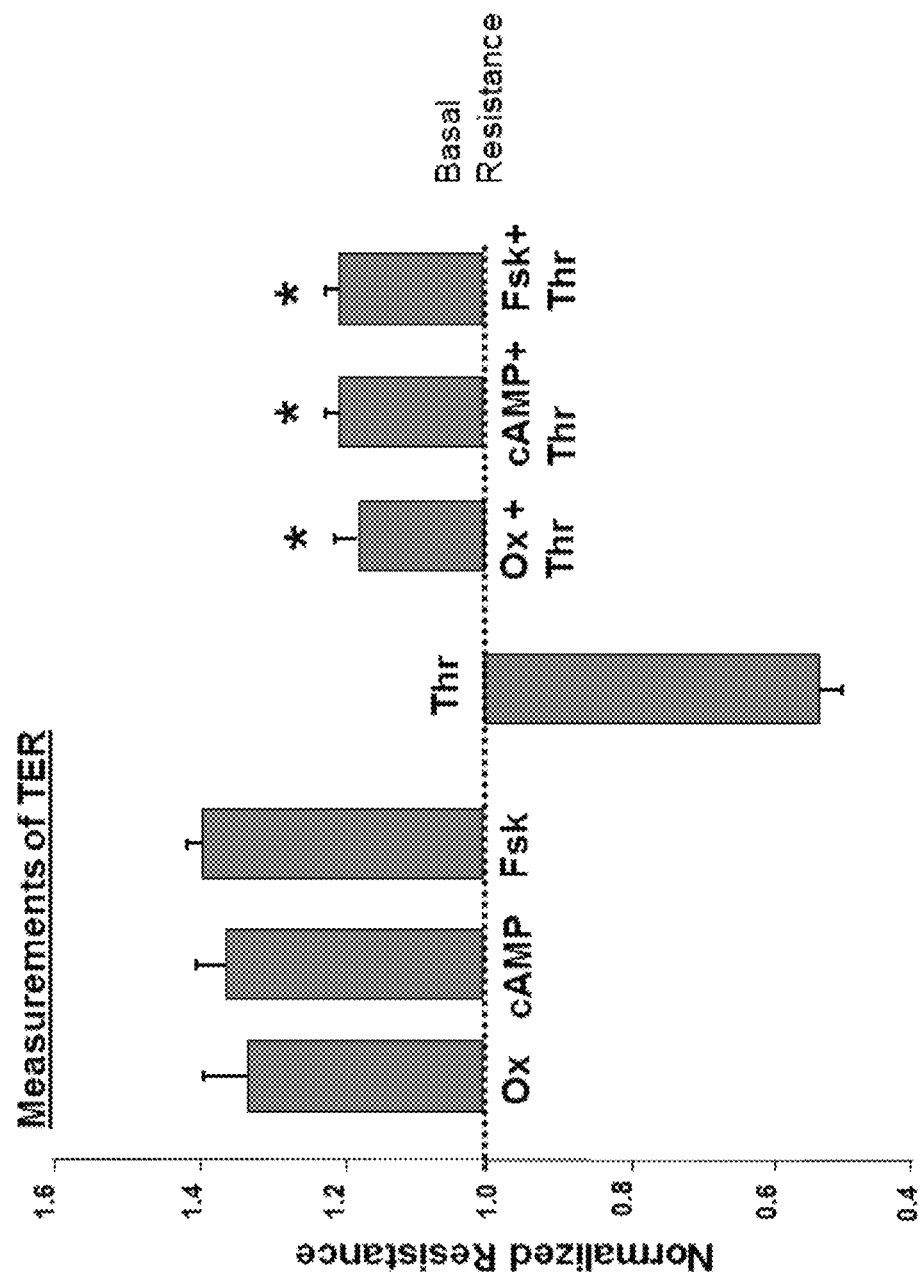

An endothelial cell monolayer maintains a basal level of permeability, which can be dynamically regulated by pathologic and physiologic stimuli. Adaptation of the XPerT method to a 96-well format allows analysis of time-dependent permeability responses in one assay. Thrombin stimulation was used as an established model of agonist-induced endothelial barrier compromise and led to the time-dependent and reversible increase in substrate-associated FITC fluorescence reflecting increased permeability (FIG. 3A).

The high throughput format of this assay allows for rapid simultaneous measurements of cell monolayer permeability changes induced by a variety of bioactive molecules and their combinations. The capacity of this method to simultaneously analyze both the barrier-disruptive and barrier-enhancing cell responses to various agonists and their combination was further tested.

Enhancement of endothelial monolayer barrier properties by oxidized phospholipids (OxPAPC) or elevation of intracellular cyclic AMP levels using 8Br-cAMP and forskolin has been previously demonstrated using transwell assays and transendothelial electrical resistance measurements (Birukov et al., 2004; Fukuhara et al., 2005). Results were compared of human endothelial cell permeability testing using TER measurements and the XPerT assay in 96-well format.

OxPAPC, 8Br-cAMP and forskolin significantly decreased the fluorescence signal in the XPerT assay indicating decreased monolayer permeability, while thrombin markedly increased permeability. Cell pretreatment with OxPAPC, 8Br-cAMP, and forskolin attenuated thrombin-induced permeability as detected by a decreased fluorescence signal (FIG. 3B). These results strongly correlate with independent analysis of permeability responses performed using measurements of transendothelial electrical resistance (FIG. 3C).

Example 5

XPerT Application for Permeability Visualization

None of the existing techniques allow for precise and reliable visualization of high permeability regions in a live cell monolayer. Such tools are critically important for understanding the regulation of local permeability and cell junction integrity of vascular endothelium, lung alveolocytes or intestinal epithelium, as a few examples.

Figure 4:
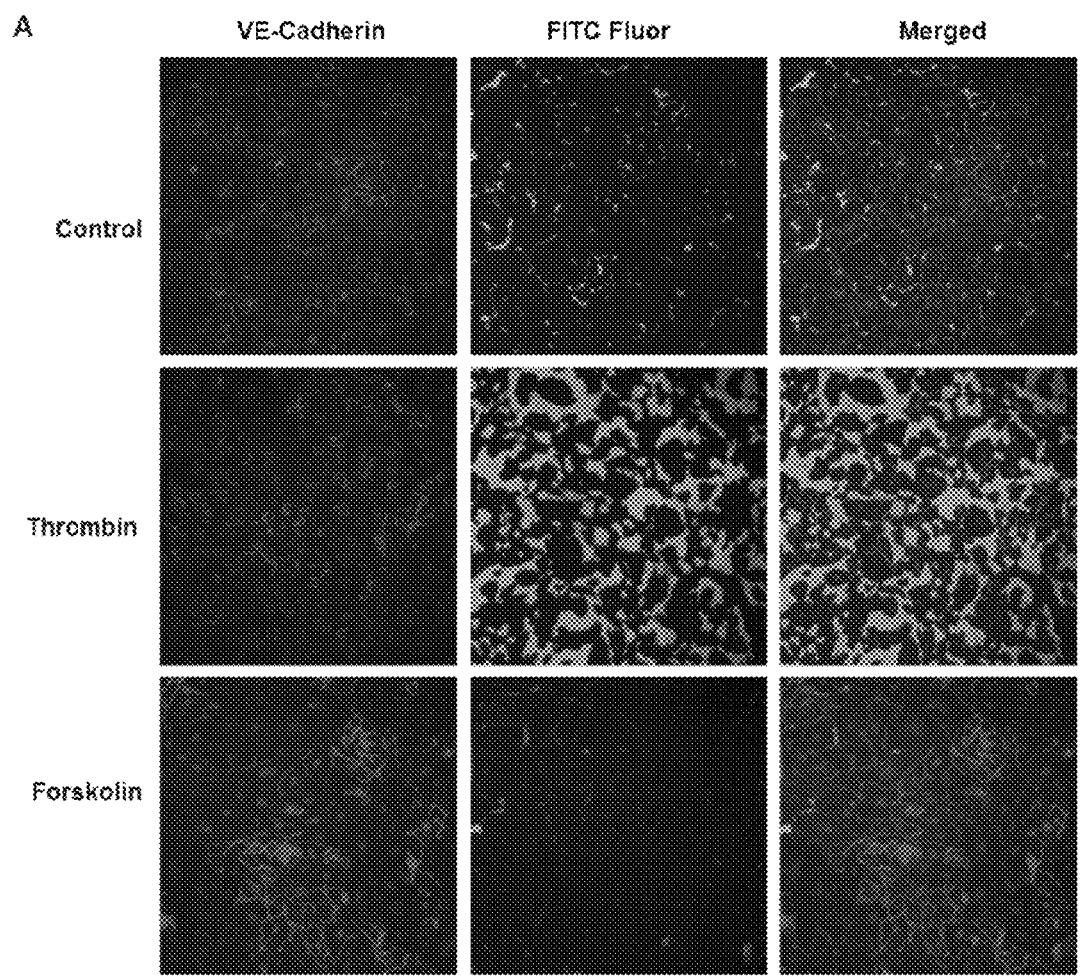
FIG. 4. Visualization of agonist-induced permeability in endothelial monolayers. A and B—HPAEC were plated on coverslips coated with biotinylated gelatin and grown to confluence. HPAEC were treated with thrombin (0.2 U/ml or 0.3 U/ml, 15 min) or forskolin (2 µM, 30 min). At the end of the experiment, FITC-avidin was added for 3 min, cells were fixed and subjected to immunfluorescence staining for VE-cadherin (red) to visualize cell-cell contacts. Green fluorescence depicts areas permeable for FITC-labeled avidin. Images were taken using 10× (A) and 60× (B) objectives. C—Intercellular gap closure during HPAEC growth was monitored by decreased number of FITC-positive intercellular spots after 24, 48, and 72 hours of cell culture.
Figure 4:
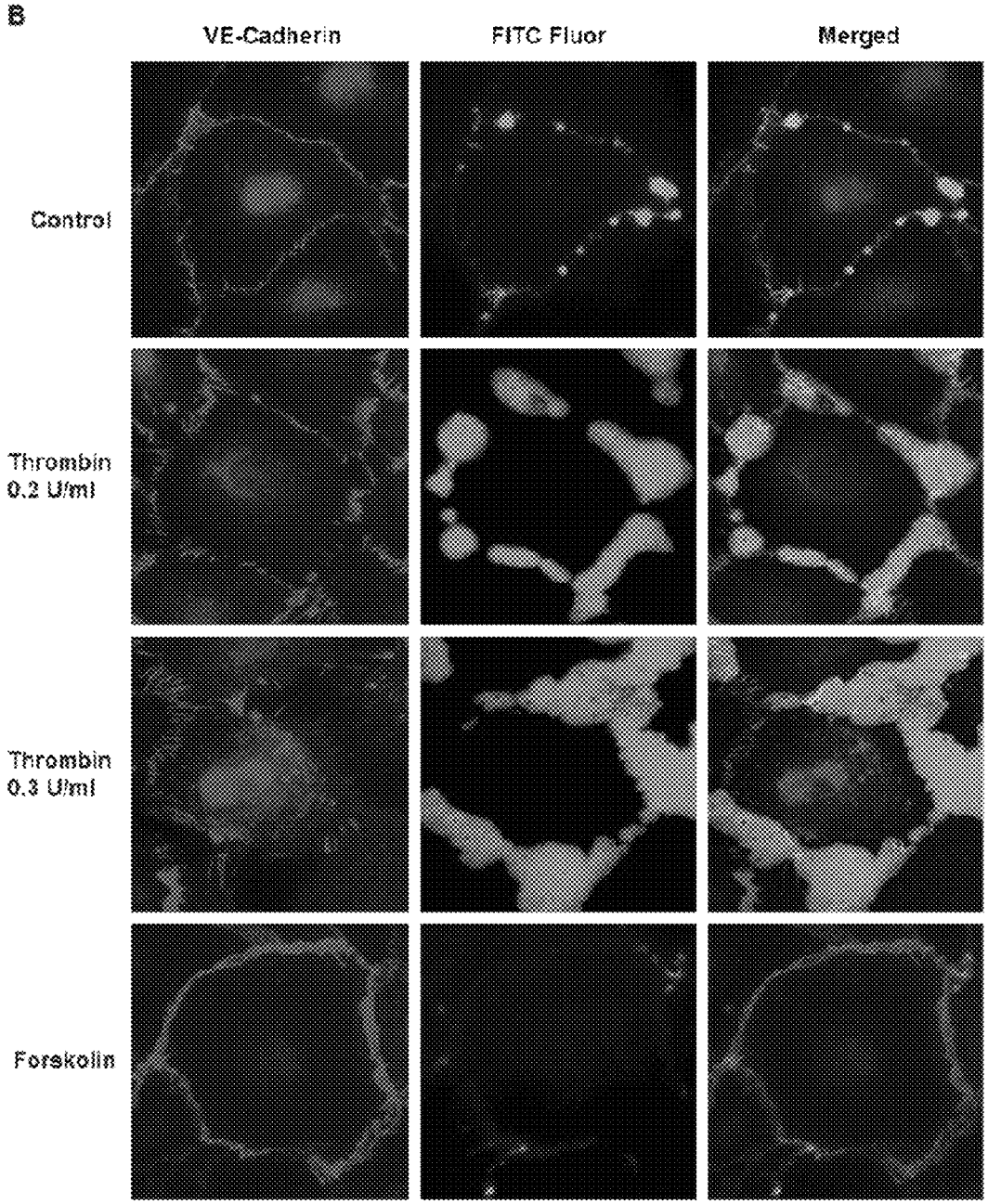
Figure 4:
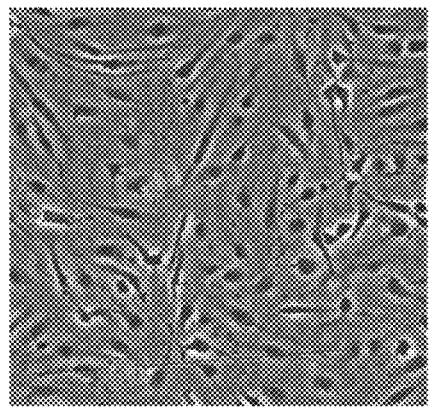
Figure 4:
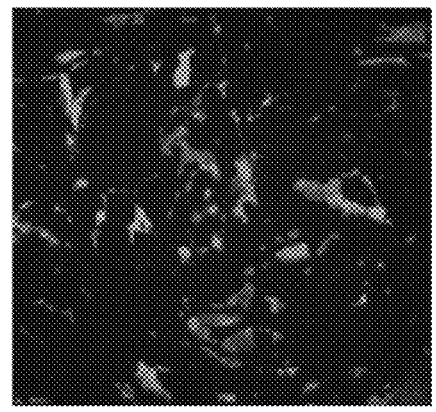
Figure 4:
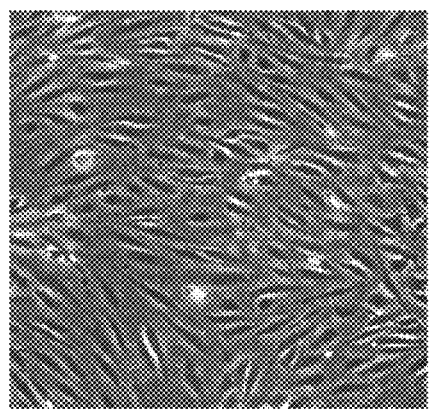
Figure 4:
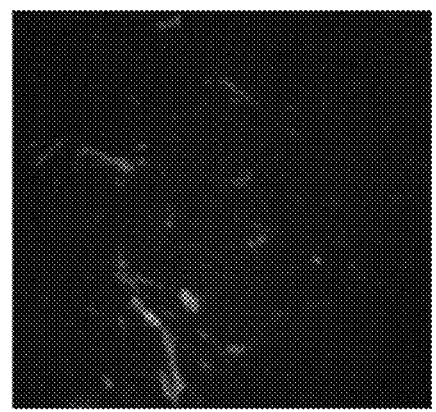
Figure 4:
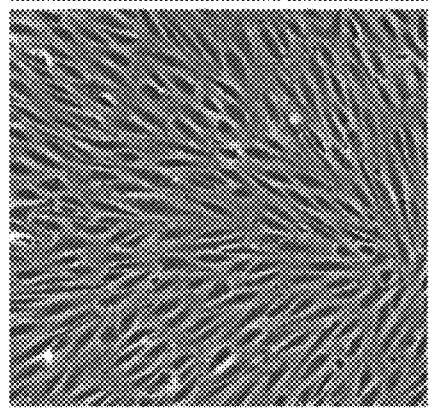
Figure 4:
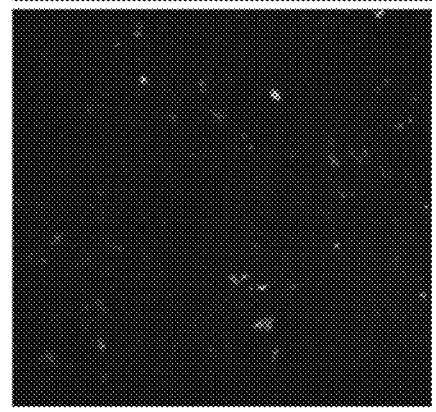

Local permeability changes induced by thrombin and forskolin were visualized in cells grown on biotinylated gelatin plastic coverslips. The pattern of FITC-avidin binding to the biotinylated gelatin underlying the cell monolayer was examined under a microscope (FIG. 4A). The structural integrity of cell-cell junctions was evaluated in control and agonist stimulated cell monolayer after FITC-avidin incubation by immunostaining of the adherens junction protein VE-cadherin. Low magnification images demonstrate minimal FITC fluorescence accumulation at the cell-cell junction areas of control cell monolayer, further barrier preservation in forskolin-treated cells, and a dramatic increase in FITC fluorescence in the intercellular gaps upon thrombin treatment (FIG. 4A). Overlay of FITC and VE-cadherin staining demonstrates reciprocal relations between VE-cadherin peripheral localization and increased local permeability of FITC-avidin.

This novel assay also allows for high resolution visualization of permeability sites in the cell monolayer and their relation to local changes in cytoskeletal or cell adhesion structure. Basal permeability of non-stimulated pulmonary endothelium can be seen as a thin ring of FITC-avidin fluorescence surrounding cells with a few larger pores indicating increased local permeability (FIG. 4B, upper row). Thrombin treatment caused a dose-dependent, non-uniform increase in intercellular permeability reflected by enlarged areas of intercellular fluorescence (FIG. 4B, middle rows). In contrast, forskolin diminished basal permeability levels. These changes were associated with enlargement of cell-cell junction complexes detected by VE-cadherin staining (FIG. 4B, lower row).

The stability of biotinylated gelatin or collagen matrices immobilized on culture dishes (characterized in FIG. 2B) also allows for evaluation of monolayer permeability over the course of several days. Therefore, the XPerT assay can be used to monitor the confluency state of the cell monolayer in chronic experiments (FIG. 4C).

Figure 5:
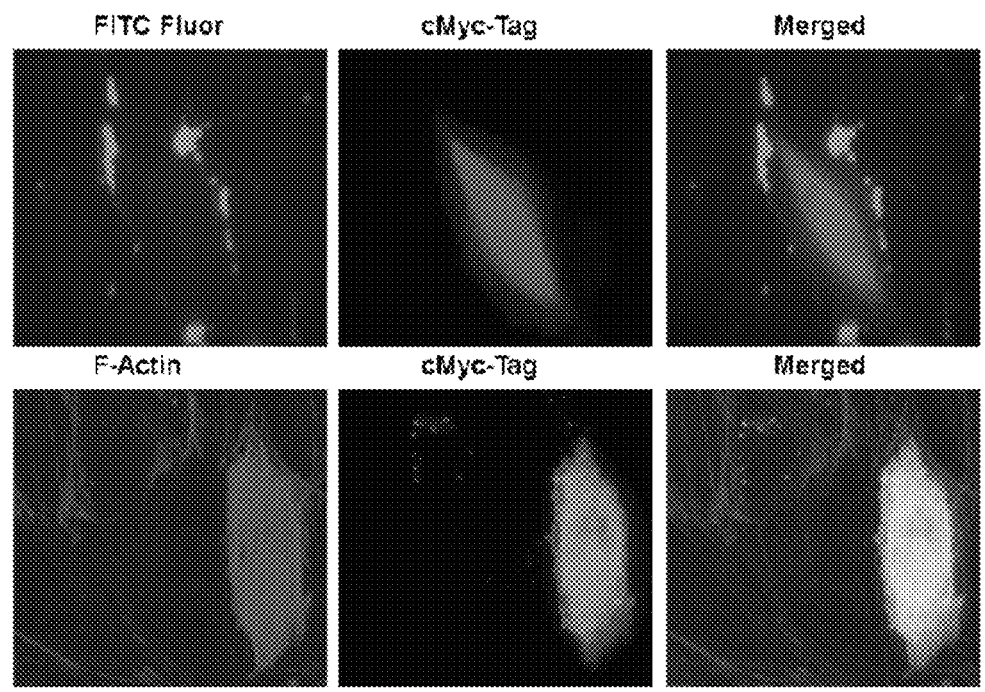
FIG. 5. Visualization of local cell permeability. HPAEC seeded on biotinylated gelatin coated coverslips were transfected with A—cMyc-tagged activated Rho kinase-CA or B—cMyc-tagged RhoA-V14 mutant followed by incubation with FITC-avidin and immunofluorescence staining for cMyc tag (red). Green fluorescence depicts areas permeable to FITC-labeled avidin. Merged images show areas of increased local permeability surrounding cells expressing activated RhoA. Lower panels depict staining of F-actin with Texas-Red phalloidin (red) and cMyc tag (green) performed in parallel experiments. Cytoskeletal staining detects large paracellular gaps but does not distinguish precise spots of increased permeability.
Figure 5:
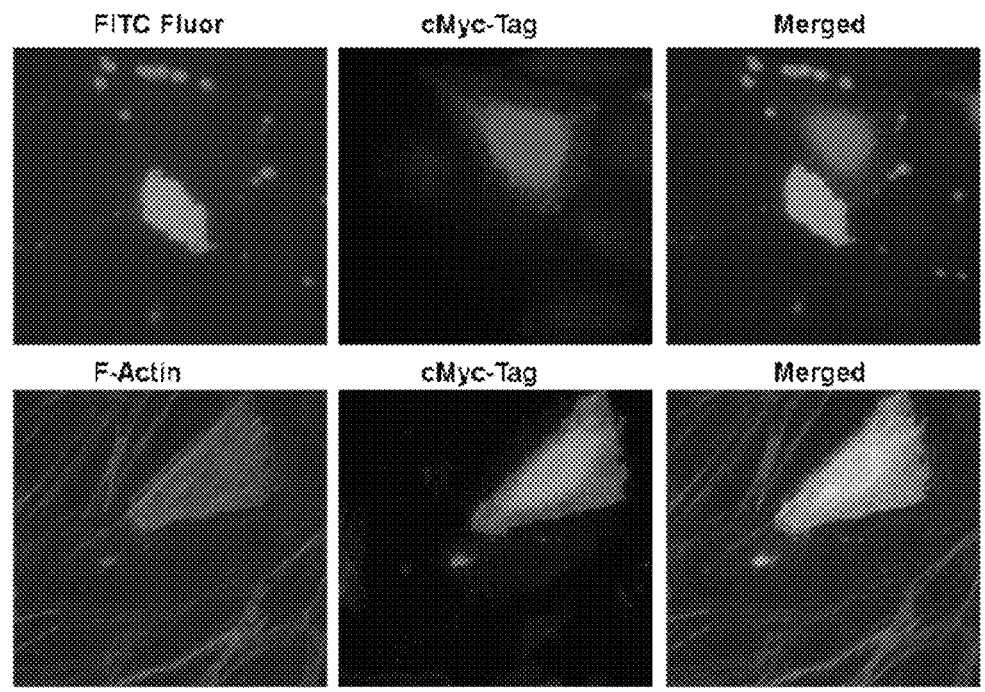

A major limitation of existing molecular approaches to dissect pathways regulating cell permeability is the inability to visualize local permeability rendered by transfected cells within the intact monolayer. The suitability of the XPerT method to address this problem was tested in cells transiently transfected with constitutively activated Rho kinase (Rho kinase-CAT), or the activated RhoA mutant (RhoA-V14). These activated proteins increased endothelial permeability (van Nieuw Amerongen et al., 2000; Wojciak-Stothard et al., 2002). Increased permeability was observed in the area surrounding cells expressing activated Rho kinase (FIG. 5A) and activated RhoA (FIG. 5B). No changes in local permeability can be seen in non-transfected cells (FIG. 5AB, top panels) or cells transfected with control vector (data not shown). In comparison, cytoskeletal staining of transfected and non-transfected cells in monolayer cultures did not provide reliable visualization of the areas with increased permeability (FIG. 5AB, bottom panels).

Example 6

XPerT: Permeability Measurements in Cell Monolayer on Elastic Substrates Under Mechanical Stimulation The physical forces are important regulators of endothelial and epithelial barrier function (Birukov, 2009; Tzima et al., 2005; Sidhaye et al., 2008; Cohen et al., 2008), and approaches to measure permeability in cells exposed to mechanical stimulation are in high demand. Until now, such techniques were unavailable. To overcome this methodological constraint, the application of the XPerT assay to the flexible-bottomed culture plates that can be used for exposure of various cells to cyclic stretch was tested. The biotinylated gelatin coating protocol was adapted for silicone based stretch plates, as the first example of an elastic substrate.

Figure 6:
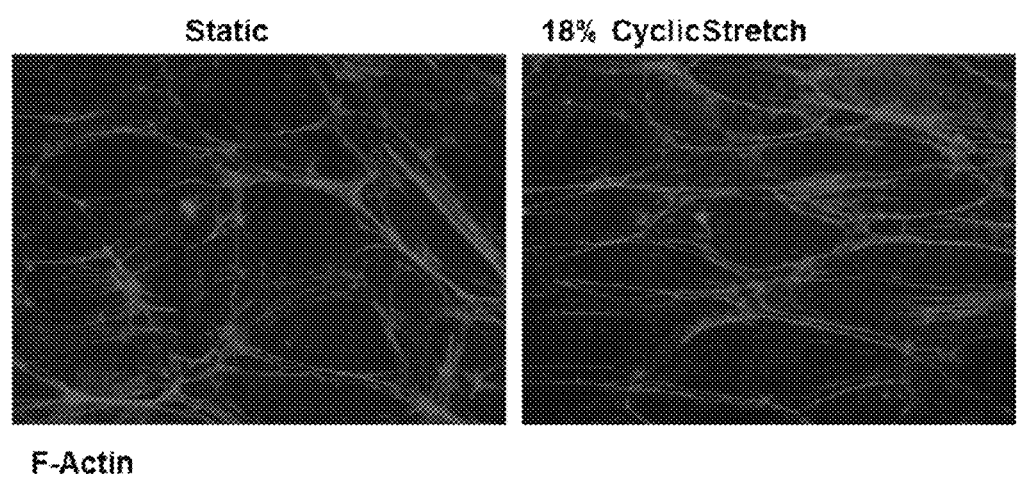
FIG. 6. Measurements of endothelial monolayer permeability under cyclic stretch. A—Confluent HPAEC grown on Flexcell plates were exposed to 18% cyclic stretch for 2 hours or left static. F-actin arrangement in static and CS-exposed cells was visualized using Texas-Red phalloidin. B—Flexcell plates coated with biotinylated gelatin were seeded with HPAEC and exposed to 18% cyclic stretch for 2 hours or left static. After two hours of stretch preconditioning, cells were stimulated with thrombin (0.3 U/ml, 15 min) or vehicle. FITC-avidin was added as described above, and FITC fluorescence of silicon bottom membranes was measured using Victor X5 plate reader. *$P<0.05$ vs. vehicle, #$P<0.05$ vs. static.
Figure 6:
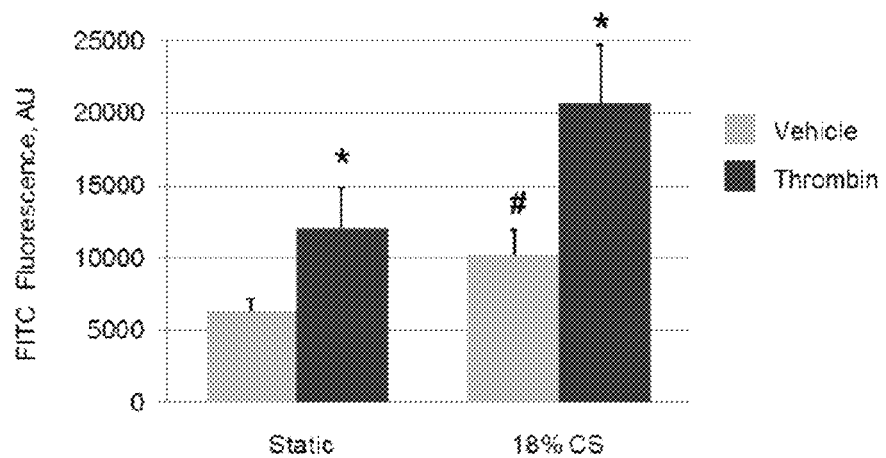

The permeability of the endothelial monolayer under static conditions and upon exposure to pathologically relevant cyclic stretch magnitude (18% CS)(Birukova et al., 2006), was further evaluated by measurement of FITC fluorescence intensity of the bottom membranes excised from the stretch plates. Two hour exposure of cells to 18% CS induces cytoskeletal reorientation without visible alterations in monolayer integrity (FIG. 6A). However, application of the CS-adapted XPerT assay allows for the first time the direct detection of increased leakiness in endothelial monolayer exposed to pathologic cyclic stretch (FIG. 6B). Thrombin treatment of static cells and cells exposed to continuous CS further increased monolayer permeability. These experiments illustrate a significant advancement in existing approaches for evaluation of monolayer barrier properties in static and a mechanically active environment, which have been previously possible only by means of morphometric analysis of visible cell-denuded areas ((Birukova et al., 2006; Crosby et al., 2011).

Example 7

Significance of Certain Embodiments

Methods and compositions set forth a novel embodiment for a cell permeability assay based on high affinity ligand-acceptor interactions and describe several applications of this methodology for analysis of novel aspects of monolayer permeability. Monolayer permeability can be evaluated by this method in bulk assays using quantification of fluorescence by a microplate reader, or may engage fluorescence microscopy and image analysis to determine spatial distribution of permeability sites in a cell monolayer.

While the role of specific cytoskeletal patterns of remodeling and rearrangements in cell junction complexes have been linked to alterations of EC monolayer permeability (Mehta and Malik, 2006), direct comparison of cytoskeletal remodeling by cell monolayers with areas of increased leakiness has not been previously made possible. Permeability maps obtained using the XPerT approach from microscopic images of cells under physiologic and pathologic conditions may be further used for quantitative permeability analysis. The Examples demonstrate for the first time the reciprocal patterns of local permeability detected by the XPerT assay and heterogenous distribution of VE-cadherin, the protein playing a major role in the maintenance of the endothelial barrier (Dejana et al., 2008). Another important feature of this method is its ability to evaluate local permeability at a single cell level. This feature is critical for molecular analysis of genes and proteins regulating cell-cell interactions under pathologic conditions.

Utilization of the XPert approach for permeability analysis in EC monolayers grown on stretchable substrates has been further tested herein. This approach allowed for the first time the assessment of basal permeability of endothelial monolayers under continuous pathologic cyclic stretch, which cannot be achieved using other existing approaches. Integration of mechanotransduction studies linking mechanochemical signaling pathways with analysis of stretch-induced monolayer permeability changes will bring new dimensions in this area of research and will bridge in vitro studies and animal models of disease.

Adaptations to the assay may be employed, for example. First, substrate coating techniques can be adapted to glass surfaces, which can provide superior image quality, or other substrates currently used in tissue engineering and cell biology. The XPerT platform can be also incorporated in the microfluidics devices. Second, the versatility of the XPerT platform can be further expanded by testing a variety of other high affinity binary compounds. Examples include high affinity Fc fragment—protein A or GST—Glutathione interactions. Alternatively, utilization of substrate—enzyme pairs may significantly increase the sensitivity of such assays and allow permeability analysis in real time using fluorometric or spectrophotometric detection methods.

Thus, the novel approach for visualization and quantitation of local permeability at the subcellular level in cell cultures exposed to static or pathologic cyclic stretch conditions introduces a new dimension into studies of pathologies associated with disruption of monolayer integrity and increased permeability under dynamic mechanochemical microenvironments (Birukova et al., 2006; Cavanaugh and Margulies, 2002; Waters and Salva, 1999; Makena et al., 2010). Provided herein for the first time is direct evidence that local activation of Rho signaling caused by overexpression of constitutively active Rho GTPase or Rho kinase in pulmonary EC caused a local increase in permeability. The Examples above demonstrated direct effects of pathologic cyclic stretch on EC monolayer permeability and observed synergistic effects of pathologic cyclic stretch and thrombin on EC permeability increase, which previously was only performed indirectly, via analysis of visible gap formation. These experiments reproduce the pathologic mechanochemical environment experienced by pulmonary vascular endothelium in clinical settings of VILI/ARDS (Maniatis et al., 2008; Lionetti et al., 2005; Matthay et al., 2003). The methods and compositions at least will help overcome existing limitations faced by investigators studying molecular mechanisms of mechanotransduction, barrier regulation by pathologic mechanical forces, and preservation of monolayer integrity in health and disease.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

REFERENCES

Balda M S, Whitney J A, Flores C, Gonzalez S, Cereijido M, Matter K. Functional dissociation of paracellular permeability and transepithelial electrical resistance and disruption of the apical-basolateral intramembrane diffusion barrier by expression of a mutant tight junction membrane protein. *J Cell Biol* 1996; 134(4):1031-1049.

Birukov K G, Bochkov V N, Birukova A A, Kawkitinarong K, Rios A, Leitner A, et al. Epoxycyclopentenone-containing oxidized phospholipids restore endothelial barrier function via Cdc42 and Rac. *Circ Res* 2004; 95(9):892-901.

Birukov K G. Small GTPases in mechanosensitive regulation of endothelial barrier. *Microvasc Res* 2009; 77(1):46-52.

Birukova A A, Chatchavalvanich S, Rios A, Kawkitinarong K, Garcia J G, Birukov K G. Differential regulation of pulmonary endothelial monolayer integrity by varying degrees of cyclic stretch. *Am J Pathol* 2006; 168(5):1749-1761.

Birukova A A, Fu P, Xing J, Yakubov B, Cokic I, Birukov K G. Mechanotransduction by GEF-H1 as a novel mechanism of ventilator-induced vascular endothelial permeability. *Am J Physiol Lung Cell Mol Physiol* 2010; 298(6):L837-848.

Cavanaugh K J, Jr., Margulies S S. Measurement of stretch-induced loss of alveolar epithelial barrier integrity with a novel in vitro method. *Am J Physiol Cell Physiol* 2002; 283(6):C1801-1808.

Cohen T S, Cavanaugh K J, Margulies S S. Frequency and peak stretch magnitude affect alveolar epithelial permeability. *Eur Respir J* 2008; 32(4):854-861.

Crosby L M, Luellen C, Zhang Z, Tague L L, Sinclair S E, Waters C M. Balance of life and death in alveolar epithelial type II cells: proliferation, apoptosis, and the effects of cyclic stretch on wound healing. *Am J Physiol Lung Cell Mol Physiol* 2011; 301(4):L536-546.

Dejana E, Orsenigo F, Lampugnani M G. The role of adherens junctions and VE-cadherin in the control of vascular permeability. *J Cell Sci* 2008; 121(Pt 13):2115-2122.

Fishel R S, Are C, Barbul A. Vessel injury and capillary leak. *Crit Care Med* 2003; 31(8 Suppl):S502-511.

Fraser P A. The role of free radical generation in increasing cerebrovascular permeability. *Free Radic Biol Med* 2011; 51(5):967-977.

Fukuhara S, Sakurai A, Sano H, Yamagishi A, Somekawa S, Takakura N, et al. Cyclic AMP potentiates vascular endothelial cadherin-mediated cell-cell contact to enhance endothelial barrier function through an Epac-Rap1 signaling pathway. *Mol Cell Biol* 2005; 25(1):136-146.

Giaever I, Keese C R. Monitoring fibroblast behavior in tissue culture with an applied electric field. *Proc Natl Acad Sci USA* 1984; 81(12):3761-3764.

Green N M. Avidin. 3. The Nature of the Biotin-Binding Site. *Biochem J* 1963; 89:599-609.

Hirase T, Node K. Endothelial dysfunction as a cellular mechanism for vascular failure. *Am J Physiol Heart Circ Physiol* 2012; 302(3):H499-505.

Le Guelte A, Dwyer J, Gavard J. Jumping the barrier: VE-cadherin, VEGF and other angiogenic modifiers in cancer. *Biol Cell* 2011; 103(12):593-605.

Lionetti V, Recchia F A, Ranieri V M. Overview of ventilator-induced lung injury mechanisms. *Curr Opin Crit Care* 2005; 11(1):82-86.

Lo C M, Keese C R, Giaever I. Cell-substrate contact: another factor may influence transepithelial electrical resistance of cell layers cultured on permeable filters. *Exp Cell Res* 1999; 250(2):576-580.

Makena P S, Luellen C L, Balazs L, Ghosh M C, Parthasarathi K, Waters C M, et al. Preexposure to hyperoxia causes increased lung injury and epithelial apoptosis in mice ventilated with high tidal volumes. *Am J Physiol Lung Cell Mol Physiol* 2010; 299(5):L711-719.

Maniatis N A, Kotanidou A, Catravas J D, Orfanos S E. Endothelial pathomechanisms in acute lung injury. *Vascul Pharmacol* 2008; 49(4-6):119-133.

Matthay M A, Zimmerman G A, Esmon C, Bhattacharya J, Coller B, Doerschuk C M, et al. Future research directions in acute lung injury: summary of a National Heart, Lung, and Blood Institute working group. *Am J Respir Crit Care Med* 2003; 167(7):1027-1035.

McVerry B J, Peng X, Hassoun P M, Sammani S, Simon B A, Garcia J G. Sphingosine 1-phosphate reduces vascular leak in murine and canine models of acute lung injury. *Am J Respir Crit Care Med* 2004; 170(9):987-993.

Mehta D, Malik A B. Signaling mechanisms regulating endothelial permeability. *Physiol Rev* 2006; 86(1):279-367.

Sidhaye V K, Schweitzer K S, Caterina M J, Shimoda L, King L S. Shear stress regulates aquaporin-5 and airway epithelial barrier function. *Proc Natl Acad Sci USA* 2008; 105(9):3345-3350.

Tzima E, Irani-Tehrani M, Kiosses W B, Dejana E, Schultz D A, Engelhardt B, et al. A mechanosensory complex that mediates the endothelial cell response to fluid shear stress. *Nature* 2005; 437(7057):426-431.

van Nieuw Amerongen G P, van Delft S, Vermeer M A, Collard J G, van Hinsbergh V W. Activation of RhoA by thrombin in endothelial hyperpermeability: role of Rho kinase and protein tyrosine kinases. *Circ Res* 2000; 87(4): 335-340.

Ware L B, Matthay M A. Clinical practice. Acute pulmonary edema. *N Engl J Med* 2005; 353(26):2788-2796.

Waters C M, Savla U. Keratinocyte growth factor accelerates wound closure in airway epithelium during cyclic mechanical strain. *J Cell Physiol* 1999; 181(3):424-432.

Wojciak-Stothard B, Ridley A J. Rho GTPases and the regulation of endothelial permeability. *Vascul Pharmacol* 2002; 39(4-5):187-199.

What is claimed is:

1. An in vitro method for measuring the degree of permeability of an endothelial cell monolayer, comprising the following steps in the order listed:

providing a substrate having a matrix, the endothelial cell monolayer, and a plurality of first binding pair members associated with the matrix, wherein the matrix is contiguous with the substrate and the endothelial cell monolayer is in direct contact with the matrix and with the plurality of first binding pair members associated with the matrix, wherein the matrix and first binding pair members are positioned between the monolayer and the substrate;

subjecting the substrate to mechanical stimulation by stretching the substrate;

contacting the cell monolayer with a plurality of labeled second binding pair members; wherein the first and second binding pair members are separated by the cell monolayer; and detecting the amount of binding of a plurality of first binding pair members to a plurality of second binding pair members by visualizing the label through the side of the substrate that is opposite the matrix, wherein the degree of permeability is determined from the amount of binding of the first binding pair members to the second binding pair members; and wherein the first binding pair members are biotin and the second binding pair members are streptavidin.

2. The method of claim 1, wherein the amount of binding is detected in more than one region of the cell monolayer.

3. The method of claim 2, further comprising detecting the presence or absence of differential permeability in different regions of the cell monolayer comprising comparing the amount of binding in the regions of the cell monolayer; wherein a difference in the amount of binding in the regions indicates a presence of differential permeability and wherein the same amount of binding in the regions indicates and absence of differential permeability.

4. The method of claim 1, wherein the stretching of the substrate is performed cyclically.

5. The method of claim 1, further comprising exposing the cell monolayer to a compound that detects a cell junction protein.

6. The method of claim 1, wherein the permeability that is measured is intercellular permeability.

7. The method of claim 1, wherein the permeability that is measured is transcellular permeability.

8. The method of claim 1, wherein the substrate is impermeable.

9. The method of claim 1, wherein the substrate is made of glass, metal, or a silicone-based material.

10. The method of claim 1, wherein the substrate is a culture dish, slide, well, cover slip, stretch or flow chamber, or elastic substrate.

11. The method of claim 1, further comprising the step of exposing a test substance to the cell monolayer before the amount of binding is detected.

12. The method of claim 11, wherein binding is detected between five minutes and five days after exposing the test substance to the cell monolayer.

* * * * *

UNITED STATES PATENT AND TRADEMARK OFFICE
CERTIFICATE OF CORRECTION

PATENT NO.        : 9,588,106 B2
APPLICATION NO.   : 14/019055
DATED             : March 7, 2017
INVENTOR(S)       : Oleksii Dubrovskyi et al.

It is certified that error appears in the above-identified patent and that said Letters Patent is hereby corrected as shown below:

In the Claims

In Column 24 on Line 33, --indicates and-- should read "indicates an".

Signed and Sealed this
Twenty-fifth Day of April, 2017

Michelle K. Lee
*Director of the United States Patent and Trademark Office*